US011076616B2

(12) United States Patent
Oelmann et al.

(10) Patent No.: US 11,076,616 B2
(45) Date of Patent: Aug. 3, 2021

(54) L-AMINO ACID-CONTAINING FEEDSTUFF ADDITIVE

(71) Applicant: Evonik Operations GmbH, Essen (DE)

(72) Inventors: Ansgar Oelmann, Gelnhausen (DE); Hans Christian Alt, Gelnhausen (DE); Franz Ulrich Becker, Freigericht-Horbach (DE); Wilfried Blümke, Schöneck (DE); Wilfried Claes, Bielefeld (DE)

(73) Assignee: Evonik Operations GmbH, Essen (DE)

( * ) Notice: Subject to any disclaimer, the term of this patent is extended or adjusted under 35 U.S.C. 154(b) by 506 days.

(21) Appl. No.: 15/031,260

(22) PCT Filed: Oct. 6, 2014

(86) PCT No.: PCT/EP2014/071309
§ 371 (c)(1),
(2) Date: Apr. 21, 2016

(87) PCT Pub. No.: WO2015/058949
PCT Pub. Date: Apr. 30, 2015

(65) Prior Publication Data
US 2016/0255863 A1 Sep. 8, 2016

(30) Foreign Application Priority Data
Oct. 24, 2013 (EP) .................................... 13190052

(51) Int. Cl.
| | |
|---|---|
| *A23K 20/142* | (2016.01) |
| *A23K 40/10* | (2016.01) |
| *A23K 20/158* | (2016.01) |
| *C12P 13/12* | (2006.01) |
| *C12P 13/08* | (2006.01) |
| *C12P 13/22* | (2006.01) |
| *A23K 40/30* | (2016.01) |
| *A23K 10/12* | (2016.01) |
| *A23K 20/20* | (2016.01) |

(52) U.S. Cl.
CPC ............ *A23K 20/142* (2016.05); *A23K 10/12* (2016.05); *A23K 20/158* (2016.05); *A23K 20/20* (2016.05); *A23K 40/10* (2016.05); *A23K 40/30* (2016.05); *C12P 13/08* (2013.01); *C12P 13/12* (2013.01); *C12P 13/22* (2013.01)

(58) Field of Classification Search
CPC .... A23K 20/142; A23K 20/158; A23K 20/20; A23K 40/10; A23K 40/30; A23K 10/12; C12P 13/08; C12P 13/12; C12P 13/22
See application file for complete search history.

(56) References Cited

U.S. PATENT DOCUMENTS

| | | | |
|---|---|---|---|
| 3,541,204 A | 11/1970 | Linton | |
| 3,615,681 A * | 10/1971 | DuRoss | A21D 2/16 426/24 |
| 3,759,789 A * | 9/1973 | Watanabe et al. | C12P 13/06 435/115 |
| 4,275,157 A | 6/1981 | Tosaka et al. | |
| 5,275,940 A | 1/1994 | Kino et al. | |
| 5,431,933 A | 7/1995 | Binder et al. | |
| 5,567,606 A * | 10/1996 | Hayashi | B01D 19/0404 252/182.27 |
| 5,622,710 A * | 4/1997 | Binder | A23K 40/10 424/438 |
| 5,770,409 A | 6/1998 | Pfefferle et al. | |
| 5,840,358 A * | 11/1998 | Hofler | B01J 2/16 426/467 |
| 5,840,551 A | 11/1998 | Werning et al. | |
| 5,990,350 A | 11/1999 | Stevens et al. | |
| 6,013,286 A | 1/2000 | Klose | |
| 6,238,728 B1 | 5/2001 | Ishiguri et al. | |
| 6,451,903 B1 | 9/2002 | Asano et al. | |
| 6,756,510 B1 | 6/2004 | Binder et al. | |
| 6,797,291 B2 | 9/2004 | Richardson | |
| 7,416,740 B2 | 8/2008 | Kushiki et al. | |
| 7,521,080 B2 * | 4/2009 | Alt | B01J 2/16 426/453 |
| 8,580,853 B2 | 11/2013 | Phykitt | |
| 8,802,400 B2 | 8/2014 | Lotter et al. | |
| 9,023,347 B2 | 5/2015 | Lotter et al. | |
| 2003/0165611 A1 | 9/2003 | Chiavazza | |
| 2004/0115304 A1 | 6/2004 | Dubner et al. | |
| 2007/0082031 A1 | 4/2007 | Lotter et al. | |

(Continued)

FOREIGN PATENT DOCUMENTS

| | | |
|---|---|---|
| CN | 102442919 | 5/2012 |
| DE | 10 2006 016 158 | 4/2007 |

(Continued)

OTHER PUBLICATIONS

English language translation of the International Preliminary Report on Patentability for corresponding international application PCT/EP2014/071309 filed Oct. 6, 2014.
Ozaki, et al., "Production of Lysine by Pyruvate Kinase Mutants of *Brevibacterium flavum,*" *Agric. Biol. Chem.* 47(7):1569-1576 (Jan. 1983).
English language translation of the International Search Report for corresponding international application PCT/EP2014/071309 filed Oct. 6, 2014.
English language translation of the Written Opinion of the International Searching Authority for corresponding international application PCT/EP2014/071309 filed Oct. 6, 2014.

(Continued)

*Primary Examiner* — Walter A Moore
(74) *Attorney, Agent, or Firm* — Law Office of Michael A. Sanzo, LLC

(57) ABSTRACT

By substituting biomass with a surface-active substance in a fermentation broth containing amino acid before spray-drying, granulated animal feed additives with improved product specifications were obtained.

20 Claims, No Drawings

(56) References Cited

U.S. PATENT DOCUMENTS

| | | |
|---|---|---|
| 2007/0292919 A1 | 12/2007 | Holt et al. |
| 2009/0092704 A1 | 4/2009 | Gately |
| 2009/0280542 A1 | 11/2009 | Bathe et al. |
| 2009/0311758 A1 | 12/2009 | Jessberger et al. |
| 2010/0261257 A1 | 10/2010 | Bathe et al. |
| 2010/0310714 A1 | 12/2010 | Lotter et al. |
| 2016/0255862 A1 | 9/2016 | Oelmann et al. |

FOREIGN PATENT DOCUMENTS

| | | | |
|---|---|---|---|
| EP | 0 288 779 | 7/1987 | |
| EP | 0 923 878 | 6/1996 | |
| EP | 0 743 016 | 11/1996 | |
| EP | 1 331 220 | 7/2003 | |
| EP | 1 360 904 | 11/2003 | |
| EP | 1 752 543 | 2/2007 | |
| GB | 1217365 A | * 12/1970 | ........... A61K 9/1611 |
| GB | 1 439 121 | 6/1976 | |
| GB | 1 439 728 | 6/1976 | |
| GB | 2 293 304 | 3/1996 | |
| WO | WO 2004/054381 | 7/2004 | |
| WO | WO 2007/141111 | 12/2007 | |

OTHER PUBLICATIONS

European Search Report for EP 13 19 0052, (priority application to corresponding international application PCT/EP2014/071309 filed Oct. 6, 2014.), with partial machine translation attached.

English language translation of the International Search Report for international application PCT/EP2014/071329 filed Oct. 6, 2014 (corresponds to copending U.S. Appl. No. 15/031,258).

English language translation of the Written Opinion of the International Searching Authority for international application PCT/EP2014/071329 filed Oct. 6, 2014 (corresponds to copending U.S. Appl. No. 15/031,258).

English language translation of the International Preliminary Report on Patentability for international application PCT/EP2014/071329 filed Oct. 6, 2014 (corresponds to copending U.S. Appl. No. 15/031,258).

European Search Report for EP 13 19 0055, (priority application for international application PCT/EP2014/071329 filed Oct. 6, 2014), with partial machine translation attached.

Shiio, et al., "Studies on Mechanisms for Lysine Production by Pyruvate Kinase-Deficient Mutants of *Brevibacterium flavum*," *Agric. Biol. Chem. 48*(6):1551-1558 (Dec. 1983).

Epand, et al., "Bacterial lipid composition and the antimicrobial efficacy of cationic steroid compounds (Ceragenins)," *Biochimica et Biophysica Acta 1768*:2500-2509 (accepted May 2007).

Hull, et al., "Composition of Corn Steep Water during Steeping," *J. Agric. Food Chem. 44*:1857-1863 (Jul. 1996).

Neidhardt and Umbarger, from chapter 3 in Neidhardt F.C. *Escherichia coli* and *Salmonella*: Cellular and Molecular Biology 2nd edition, vol. 1, American Society of Microbiology (ASM) Press BioNumber Details Page and Table 1 (1996).

Printout of Wikipedia entry "Defoamer" (printed Apr. 10, 2017).

Office Action dated Sep. 28, 2018 for copending U.S. Appl. No. 15/031,258.

Machine translation of WO 2007/141111 (published Dec. 13, 2007).

Restriction Requirement for co-pending U.S. Appl. No. 15/031,258, dated Apr. 23, 2018.

Response to Restriction Requirement for co-pending U.S. Appl. No. 15/031,258, filed Jul. 21, 2018.

Amendment to Accompany Response to Restriction Requirement for co-pending U.S. Appl. No. 15/031,258, filed Jul. 21, 2018.

U.S. Appl. No. 15/031,258 , filed Apr. 21, 2016, US 2016/0255862 A1, Sep. 8, 2016, Oelmann.

Response to Office Action filed Feb. 27, 2019 for copending U.S. Appl. No. 15/031,258.

Office Action dated May 14, 2019 for copending U.S. Appl. No. 15/031,258.

RCE and Response to Office Action filed Sep. 3, 2019 for copending U.S. Appl. No. 15/031,258.

Office Action dated Dec. 10, 2019 for copending U.S. Appl. No. 15/031,258.

Response to Office Action filed Apr. 8, 2020 for copending U.S. Appl. No. 15/031,258.

Final Office Action dated Apr. 27, 2020 for copending U.S. Appl. No. 15/031,258.

\* cited by examiner

L-AMINO ACID-CONTAINING FEEDSTUFF ADDITIVE

CROSS REFERENCE TO RELATED APPLICATIONS

The present application is US national stage of international application PCT/EP2014/071309, which had an international filing date of Oct. 6, 2014, and which was published in German on Apr. 30, 2015. Priority is claimed to European application EP 13190052.4, filed on Oct. 24, 2013. The contents of the priority application is hereby incorporated by reference in its entirety.

The invention relates to fermentation broth-based feed additives containing L-amino acid, which comprise a surface-active substance and from which the biomass has been partially or completely removed and also methods for the preparation thereof.

PRIOR ART

Animal feeds are supplemented with individual amino acids to meet the needs of the animals. The substance which is currently predominantly employed for supplementing animal feeds, for example with L-lysine, is L-lysine monohydrochloride, with an L-lysine content of ca. 80%. Since L-lysine is produced by fermentation, it must, to prepare the monohydrochloride, first and foremost be separated in complicated method steps from all remaining constituents of the crude fermentation broth, then converted to the monohydrochloride, and the latter must be crystallized. This generates a large number of by-products and the reagents required for processing in the form of waste. Since high purity of the animal feed supplement is not always required and since, moreover, the fermentation by-products still frequently contain nutritionally effective substances of value, there has, therefore, been no lack of attempts in the past to avoid the complicated production of feed amino acids, particularly of pure L-lysine monohydrochloride, and to convert the crude fermentation broth into a solid animal feed in a more cost-effective manner.

It has emerged that the grave disadvantage is the complex composition of such media, since these media can generally only be dried with difficulty, whereupon they are hygroscopic, virtually not flowable, at risk from agglomeration, and not suited to the technically complex processing in feed mills. This applies in particular to fermentation products containing L-lysine. Simple dehydration of the crude fermentation broth by spray-drying resulted in a dusty, highly hygroscopic concentrate which agglomerated after a brief storage period and which cannot be employed as animal feed in this form.

EP 0 533 039 relates to methods for preparing a fermentation broth-based amino acid animal feed supplement, wherein the supplement may be obtained directly from the fermentation broth by means of spray-drying. In one variant, some of the biomass in this case is removed before the spray-drying step.

GB 1 439 121 discloses solid concentrates which contain ca. 20% by weight of L-lysine, and this specification also describes fermentation broths containing L-lysine with a pH of 4.5 and the addition of sodium bisulphite.

EP 0 615 693 discloses a method for preparing a fermentation broth-based animal feed additive, in which the fermentation broth, optionally after removal of some of the constituents, is spray-dried to give fine particles of which at least 70% by weight have a maximum particle size of 100 μm, and in which these fine particles are enlarged in a second stage to give granules comprising the fine particles at not less than 30% by weight.

According to GB 1 439 728 a concentrate containing L-lysine is prepared from a fermentation broth, which, before concentration, is acidified with HCl to a pH of ca. 6.4 and to which bisulphite is added for stabilization purposes. After the evaporation, the product is further acidified to a pH of 4.0 and the desired product is obtained by spray-drying.

EP 1 331 220 relates to granulated feed additives which contain L-lysine as the main component. In that specification, it has been found that the amount of the counterions for the lysine, such as the amount of sulphate ions, may be reduced by using hydrogen carbonate and/or carbonate, which are/is generated during the fermentation, as the counterion. In total, an anion/lysine ratio of 0.68 to 0.95 is described.

It is said that reducing the counterions such as sulphate in the product containing L-lysine results in an improvement of the hygroscopic properties and the caking tendency.

WO 2007/141111 discloses a method for preparing a feed additive containing L-lysine, comprising the steps of fermenting an L-lysine-producing coryneform bacterium, followed by the addition of ammonium sulphate, lowering the pH to 4.9 to 5.2 by adding sulphuric acid, wherein a total sulphate/L-lysine ratio of 0.85 to 1.2 is established in the broth, concentrating and drying, preferably granulation, to afford a product with an L-lysine content of 10 to 70% by weight, determined as lysine base, based on the total amount.

It is described in EP 0809940 that the biomass originating from the fermentation in the granulation of lysine sulphate has a positive influence on the ability to granulate and also the storage and flow characteristics of the product. A complete or partial removal of the biomass is therefore advantageous in order to increase the active ingredient content. The disadvantage here is that an active ingredient content of lysine sulphate can only be adjusted within limits. In the preparation of a feed additive containing amino acid, as described in EP 0809940, the biomass originating from the fermentation is completely or partially left in the product. Pure lysine sulphate cannot be granulated owing to its strong tendency to stickiness.

The object of the present invention, therefore, was to provide a low biomass content fermentation broth which can be more easily processed and in particular more easily granulated, and also to provide a method which allows the conversion of a fermentation broth containing L-amino acid, in particular L-lysine, into a feed additive which can be more easily processed. The method should in particular provide a feed additive with improved product specifications, particularly in relation to particle size, bulk density, storage stability, flowability and/or handling qualities.

The object of the present invention was in particular also to provide a low biomass content fermentation broth containing lysine sulphate which can be more easily processed and in particular more easily granulated, and also to provide a method which allows the preparation of a low biomass content feed additive containing lysine sulphate with improved product specifications.

The object of the invention is achieved by a method in which firstly the biomass is partially or completely removed from the fermentation broth and secondly a surface-active substance is added to the fermentation broth prior to the drying process.

In addition, it has been found, surprisingly, that the reduced biomass content in combination with the surface-active component simultaneously leads to an increased granule or particle density. This essentially produces a more compact particle and an increased bulk density. Accordingly, an on-spec product with increased bulk density can be configured by a controlled biomass reduction and substitution of the biomass by a surface-active substance.

Subject Matter of the Present Invention

The present invention relates therefore to a method for preparing a feed additive, characterized in that a fermentation broth containing L-amino acid, which has a water content of 35 to 75% by weight and a content of surface-active substance of 0.025 to 20% by weight, and from which the biomass has been partially or completely removed, is converted by drying into a particulate composition.

The present invention therefore also relates to a method for preparing a fermentation broth-based feed additive containing L-amino acid, comprising the following steps:
a) providing a fermentation broth containing L-amino acid;
b) partially or completely removing the biomass from the fermentation broth;
c) adding a surface-active substance to the fermentation broth;
d) drying the resulting mixture to give a particulate composition, wherein a granulate is preferably obtained;
e) optionally coating the resulting particle with an edible oil, wherein particles are obtained which are completely or partially coated with the edible oil.

The fermentation broth containing L-amino acid is preferably obtained by fermentation of an L-amino acid-producing microorganism in an aqueous culture medium under aerobic conditions. Preferred fermentation methods according to the invention are further illustrated in detail below.

Fermentation broth is understood to mean a fermentation medium in which a microorganism has been cultivated for a certain time and at a certain temperature. The fermentation medium or the media used during the fermentation comprises/comprise all of the substances or components which ensure proliferation of the microorganism and formation of the desired amino acid.

On completion of the fermentation, the resulting fermentation broth accordingly comprises the biomass (=cell mass) of the microorganism produced as a result of the proliferation of the cells of the microorganism (e.g. coryneformes bacterium) and the L-amino acid (particularly L-lysine) formed during the fermentation, the organic by-products formed in the course of the fermentation and the constituents of the fermentation medium/fermentation media used which are not consumed by the fermentation and the ingredients such as vitamins like biotin, amino acids such as homoserine or salts such as magnesium sulphate.

Organic by-products include substances which are generated, if applicable, in addition to the target product, from the microorganisms used in the fermentation and are optionally separated. These include other L-amino acids which, compared to the desired L-amino acid (particularly L-lysine), account for less than 30%, 20% or 10%. These further include organic acids which bear one to three carboxyl groups such as acetic acid, lactic acid, citric acid, malic acid or fumaric acid. Finally, sugars such as trehalose are also included here.

Suitable fermentation broths for industrial purposes typically have an L-amino acid content (particularly L-lysine content) of 40 g/kg to 180 g/kg or 50 g/kg to 150 g/kg. The biomass content (as dried biomass) in the fermentation broth is generally 20 to 50 g/kg, but in low biomass content fermentation the biomass content can also be below this level.

The fermentation broth preferably comprises an L-amino acid selected from L-lysine, L-methionine, L-threonine, L-valine or L-tryptophan. The fermentation broth particularly preferably comprises the L-amino acid L-lysine.

In a particularly preferred embodiment according to the invention, the L-amino acid is L-lysine, wherein the method comprises an additional method step, which is carried out before the start of the drying, in which ammonium sulphate and/or sulphuric acid is added to the fermentation broth, in order to establish a sulphate/L-amino acid ratio of at least 0.5, preferably 0.85 to 1.2. This particularly preferred embodiment is further explained in detail below.

The fermentation broth used according to the invention preferably has the following properties on completion of the fermentation:
a) biomass content of 1 to 5% by weight, preferably 2 to 4.5% by weight, particularly preferably 2.5 to 3.5% by weight,
b) L-amino acid content, preferably L-lysine, (as amino acid base) of 5 to 20% by weight,
c) solids content (including biomass) of 10 to 30% by weight, preferably 15 to 25% by weight,
d) % by weight ratio of sulphate to lysine of 0.8 to 1.2;
e) pH of 3.5 to 7.0, preferably 4.0 to 5.0.

The preparation of such a fermentation broth is further described below.

"Solids content" in accordance with the invention is understood to mean the mass which remains on complete removal of the liquid. This dry mass also includes, in addition to suspended substances if applicable (such as the biomass), dissolved substances which only crystallize out or precipitate on drying. The solids content is in this respect complementary to the water or moisture content.

Before the start of the drying, the fermentation broth preferably has a water content of 35 to 70% by weight, particularly preferably 35 to 50% by weight. This water content may be adjusted, if required, particularly by evaporation of the fermentation broth, for example by means of a rotary evaporator, a thin film evaporator or a falling film evaporator, by reverse osmosis or by nanofiltration. The content of remaining biomass, if applicable, the L-amino acid content and the remaining solids content in the fermentation broth also increase accordingly during the concentration.

Before starting the drying process according to the invention, at least 30% by weight, particularly preferably at least 50% by weight, particularly at least 70% by weight, especially preferably at least 90% by weight, of the biomass is removed from the fermentation broth. This may be carried out before or after adjusting the water content as described above.

The biomass may be removed, in this case, particularly by centrifugation, filtration or decanting or by combinations of these methods. In a preferred embodiment according to the invention, the biomass is removed by ultrafiltration.

The organic by-products dissolved in the fermentation broth and the dissolved constituents of the fermentation medium (ingredients) which are not consumed remain at least in part in the product (>0%), at preferably not less than 25%, particularly preferably not less than 50% and very particularly preferably not less than 75%. Optionally, these also remain entirely (100%) or virtually entirely, i.e. >95% or >98%, in the product. In this context, "fermentation broth-based" means that the product comprises at least some of the constituents of the fermentation broth.

The "surface-active substance" in the context of the present application can be a pure substance which consists exclusively of a surface-active compound. However, it may also be a mixture of different surface-active compounds. In accordance with the invention, "surface-active substance" is however also understood to mean a component comprising a surface-active compound or a mixture of different surface-active compounds in a significant quantity. The surface-active compound(s) is/are present in the component in this case preferably in an amount of at least 3% by weight, particularly at least 5% by weight, particularly preferably at least 10% by weight. In a preferred embodiment, the surface-active compound(s) is/are present in the component at not less than 20% by weight, preferably not less than 25% by weight.

The surface-active substance in accordance with the invention is preferably selected from the group consisting of corn steep liquor, lipids, antifoaming agents and surfactants and also mixtures thereof.

The antifoaming agent is preferably selected from polysiloxane derivatives, mono- and polyglycols, phospholipids and also fatty acid glycerides.

The polysiloxane derivative can in particular take the form of a polyalkylsiloxane, especially a polydimethylsiloxane.

The polyglycol is preferably a polymer composed of oxyethylene and/or oxypropylene units, preferably a copolymer of oxyethylene and oxypropylene units, or is a compound comprising oxyethylene and/or oxypropylene units, such as a fatty acid alkylpolyglycol ester.

The phospholipid is preferably a phosphatidylcholine (lecithin).

The fatty acid glyceride may particularly take the form of a mono- or diglyceride, especially a mono- or diglyceride in which the acid residue is selected from acetic acid, lactic acid, citric acid, tartaric acid and mixtures thereof.

The corn steep liquor used according to the invention preferably has a dry mass of at least 40% by weight, preferably 45 to 55% by weight, and preferably has a residual sugar content of at most 2% by weight. Corn steep liquor comprises phosphatidylcholine as surface-active constituent.

The lipid which may be used in accordance with the invention is preferably selected from mineral oils, vegetable oils and mixtures thereof. The oil used is particularly preferably soybean oil, olive oil, silicone oil or mixtures thereof.

In a particularly preferred embodiment according to the invention, the surface-active substance used is phosphatidylcholine or a component containing phosphatidylcholine, preferably corn steep liquor.

In a preferred embodiment, the surface-active substance is added to the fermentation broth after completion of the fermentation and before the start of the drying process.

Alternatively, the surface-active substance may optionally be added to the fermentation broth already during the course of the fermentation.

As an alternative, it is also possible that the surface-active substance is already present in the fermentation medium before the start of the fermentation.

In a particularly preferred embodiment according to the invention, the surface-active substance is already present in the fermentation broth before completion of the fermentation and further surface-active substance is added to the fermentation broth after completion of the fermentation.

The surface-active substance in the fermentation broth before the start of the drying is preferably present in an amount of 0.025 to 20% by weight, 0.1 to 20% by weight, 0.2 to 20% by weight, 0.5 to 20% by weight or 1 to 20% by weight. Preferred ranges here are 0.2 to 15% by weight, 0.3 to 15% by weight, 0.5 to 15% by weight and 1 to 10% by weight.

If a polyglycol, particularly a fatty acid alkylpolyglycol ester, or a phospholipid, particularly a lecithin, or mixtures thereof, are used as surface-active substance, a concentration of surface-active substance is preferably set to 0.1 to 5% by weight, particularly 0.2 to 4% by weight, preferably 0.25 to 2% by weight.

Preference is generally given to using this amount of surface-active substance if the surface-active substance is a component which comprises at least 50% by weight, particularly at least 70% by weight, of surface-active compounds.

If corn steep liquor, optionally in combination with other surface-active substances, is used as surface-active substance, a concentration of surface-active substance is preferably set to 0.1 to 10% by weight, particularly 0.5 to 5% by weight, preferably 1 to 3% by weight.

Preference is generally given to using this amount of surface-active substance if the surface-active substance is a component which comprises less than 30% by weight, particularly 3 to 30% by weight or 3 to 20% by weight, of surface-active compounds.

In a preferred embodiment according to the invention, the fermentation broth before the start of the drying has the following properties:

a) biomass content of at most 4% by weight, particularly 0 to 4% by weight or 0.1 to 4% by weight, preferably at most 3% by weight, particularly 0 to 3% or 0.1 to 3% by weight, particularly preferably at most 2% by weight, particularly 0 to 2% by weight or 0.1 to 2% by weight, especially preferably at most 1% by weight, particularly 0 to 1% by weight or 0.1 to 1% by weight;

b) L-amino acid content, preferably L-lysine, (as amino acid base) of 12 to 48% by weight, particularly 20 to 40% by weight;

c) solids content (including biomass) of 20 to 60% by weight, preferably 30 to 50% by weight;

d) surface-active substance content of 0.025 to 20% by weight, particularly 0.1 to 20% by weight, preferably 0.3 to 15% by weight;

e) % by weight ratio of sulphate to L-amino acid, particularly L-lysine, of 0.8 to 1.2;

f) pH of 3.5 to 7.0, preferably 4.0 to 5.0.

To set a desired L-amino acid concentration in the product, an additive may be added to the fermentation broth before starting the drying process, depending on requirements, in order to increase or decrease the L-amino acid content. The additive may also alternatively and/or additionally be added during the drying or granulation process.

In order to increase the L-amino acid content, the relevant L-amino acid is preferably added in the form of a concentrate, or optionally as a largely pure substance or salt thereof, in liquid or solid form. In order to decrease the L-amino acid content, ammonium sulphate is preferably added. The additive, if used, is preferably added to the fermentation broth in an amount of 0.1 to 10% by weight, preferably 0.1 to 5% by weight, or is preferably added in an amount that adjusts the L-amino acid concentration in the final product to 40 to 60% by weight, particularly 45 to 55% by weight.

To obtain a particulate composition, the drying may be carried out particularly by freeze-drying, preferably by a spray process, particularly spray-drying or spray granulation.

Optionally, further processing steps may follow the drying performed according to the invention, in particular, one or more granulation steps, particularly if a granulate is not obtained directly from the drying process.

In a particularly preferred embodiment of the invention, however, the fermentation broth is converted directly into a granulate in one process step, such that a subsequent granulation is not necessary. The direct conversion into a granulate is preferably carried out by a spray granulation method, particularly preferably by application of a spray granulation method using a circulating fluidized bed as described in patent application WO 2005/006875.

In the spray granulation, dust formed downstream of the granulation is preferably completely or at least partially recirculated into the spray granulation chamber.

Furthermore, the granulation temperature is preferably regulated such that the inlet temperature is 200 to 300° C., preferably 250 to 275° C. and the outlet temperature is 60 to 100° C., preferably 70 to 90° C.

The granulate obtainable preferably has an L-amino acid content of 40 to 60% by weight, particularly 45 to 55% by weight, particularly preferably 48 to 52% by weight, and a water content (residual moisture content) of at most 5% by weight, preferably at most 3.5% by weight.

A particulate composition is obtained by means of the drying process which is preferably free-flowing and also can be fine-grained or coarse-grained.

The free-flowing, fine-grained powder may in turn be converted into a coarse-grained, free-flowing and largely dust-free product, which can be stored, by suitable compacting or granulating processes.

The granulates may be prepared, for example, by the methods according to EP-B 0 615 693 or EP-B 0 809 940, U.S. Pat. No. 5,840,358 or WO 2005/006875 or WO 2004/054381.

"Free-flowing" is understood to mean powders which flow out unhindered from a series of glass efflux vessels having different size outflow openings at least from a vessel having a 5 mm (millimetre) opening (Klein: Seifen, Öle, Fette, Wachse 94, 12 (1968)).

A further subject matter of the present invention is a feed additive containing a preferably granular L-amino acid, particularly L-lysine, which is obtainable by a method according to the invention.

The present invention further relates to granular feed additives comprising the following features:

a) L-amino acid content, preferably L-lysine, of at least 20% by weight, preferably 25 to 60% by weight, particularly 30 to 60 or 40 to 60% by weight, particularly preferably 45 to 55% by weight, b) mean particle diameter of 60 to 2500 μm, preferably 60 to 1500 μm;

c) biomass content of at most 8% by weight, particularly 0 to 8% by weight or 0.1 to 8% by weight, preferably at most 6% by weight, particularly 0 to 6% by weight or 0.1 to 6% by weight, particularly preferably at most 4% by weight, particularly 0 to 4% by weight or 0.1 to 4% by weight, especially preferably at most 3, 2 or 1% by weight, particularly 0 to 3% by weight, 0 to 2% by weight, 0 to 1% by weight, 0.1 to 3% by weight, 0.1 to 2% by weight or 0.1 to 1% by weight;

d) surface-active substance content of 0.04 to 35% by weight, preferably 0.15 to 30% by weight, particularly preferably 0.5 to 15% by weight;

e) preferably a water content (residual moisture) of at most 4.5% by weight, particularly at most 3.5% by weight, f) preferably a layer of edible oil coating the particle.

The stated mean particle diameter here refers to the arithmetic mean.

Feed additives according to the invention preferably have a proportion of particles of >=70, 75, 80, 90, 95, 97% by weight having a particle diameter of >63 μm to <2500 μm or a proportion of >=70, 75, 80, 85, 90, 95, 97% by weight having a particle diameter of >63 to <2000 μm or a proportion of >=70, 75, 80, 85, 90, 95, 97% by weight having a particle diameter of >100 to <1700 μm. The proportion of dust, i.e. particles having a particle size <63 μm, is preferably 20% by weight or less, 15% by weight or less, 10% by weight or less, 5% by weight or less, 3% by weight or less, 2% by weight, 0 to 1% by weight, 0.5% by weight or less.

At least 75% by weight of the particles of the composition obtained particularly preferably have a particle diameter of >63 μm to <2500 μm, preferably >63 μm to <1700 μm, particularly >63 μm to <2000 μm, wherein the proportion of the particles having a particle diameter of <63 μm is preferably 20% by weight or less.

The bulk density of the preferred products is generally 600 to 800 kg/m$^3$.

The particle size distribution is preferably measured by sieve analysis in a Hosokawa Alpine air jet sieving machine, Type 200 LS-N (sieve set: mesh sizes 20, 32, 45, 63, 100, 150, 200, 250, 280, 300, 400, 500, 600, 630, 710, 800, 1000, 1180, 1400, 1600 and 2000 μm; sieving time: 3 min.).

Alternatively, the particle size may for example also be determined by laser diffraction spectrometry. Possible methods are described in the text book "Teilchengrößenmessung in der Laborpraxis" [Particle size measurement in the laboratory] by R. H. Müller and R. Schuhmann, Wissenschaftliche Verlagsgesellschaft Stuttgart (1996) and in the text book "Introduction to Particle Technology" by M. Rhodes, Wiley & Sons (1998).

Advantageous in the granulation or compacting process is the use of customary organic or inorganic auxiliaries or carriers such as starch, gelatin, cellulose derivatives or similar substances, which are often used in food or feed processing as binding agents, gelling agents or thickeners, or other substances such as silicas, silicates (EP-A 0 743 016) or stearates.

A product with the desired particle size is optionally obtained from the resulting particulate composition or resulting granulate by sieving, rolling, dust separation, grinding or combinations thereof.

Granular feed additives according to the invention are preferably further characterized in that they are coated with an oil, as described in WO 04/054381 for example, wherein the oil is preferably selected from vegetable oil (particularly olive oil, sunflower oil, soybean oil or soybean oil/lecithin mixtures), animal oil or fat and oil obtained from microorganisms by fermentation. An increased abrasion resistance of the product and a reduction in the dust content is achieved by treatment of the surfaces with the oils mentioned.

Alternatively, the product may also be applied to a customary organic or inorganic support material known in feed processing, such as silicas, silicates, meals, brans, starches, sugars or others and/or be mixed and stabilized with customary thickeners or binders. Examples of applications and methods for this purpose are described in the literature (Die Mühle+Mischfuttertechnik [Milling and compound feed technology] 132 (1995) 49, page 817).

Finally, the product may also be finished by a coating process with film formers such as metal carbonates, silicas, silicates, alginates, stearates, starches, rubbers and cellulose ethers as described in DE-C 41 00 920.

The biomass in feed additives according to the invention preferably comprises bacteria of the genus *Corynebacterium* or the genus *Escherichia* and/or cell debris from these bacteria and particularly preferably consists largely of these.

The L-amino acid content in feed additives according to the invention is preferably at least 30% by weight, preferably at least 40% by weight, particularly 40 to 60% by weight, particularly preferably 45 to 55% by weight.

The L-amino acid in the feed additives according to the invention is preferably selected from the group consisting of L-lysine, L-methionine, L-threonine, L-tryptophan and L-valine and also mixtures thereof; particularly preferably the L-amino acid is L-lysine.

The feed additive according to the invention preferably takes the form of a fermentation broth-based feed additive.

The surface-active substance present in granular feed additives according to the invention is preferably selected from the surface-active substances mentioned above.

Provided that the surface-active substance is a polyglycol, particularly a fatty acid alkylpolyglycol ester, or a phospholipid, particularly a lecithin, or mixtures thereof, the surface-active substance in the feed additive is preferably present in an amount of 0.15 to 10% by weight, particularly 0.3 to 6% by weight, particularly preferably 0.4 to 4% by weight.

Preference is generally given to this amount of surface-active substance provided that the surface-active substance is a component which comprises at least 50% by weight, particularly at least 70% by weight, of surface-active compounds.

Provided that the surface-active substance is corn steep liquor, optionally in combination with other surface-active substances, the surface-active substance in the feed additive is preferably present in an amount of 3 to 25% by weight, particularly preferably 6 to 20% by weight.

Preference is generally given to this amount of surface-active substance provided that the surface-active substance is a component which comprises less than 30% by weight, particularly 3 to 30% or 3 to 20% by weight, of surface-active substance.

The distribution of surface-active substance in the particle is preferably homogeneous, wherein "homogeneous" is understood to mean that no major difference in concentration of the surface-active substance is found between any two fractions of the particle.

The deviation in the amount of surface-active substance in any two fractions of the particle, which can take the form, for example, of any cubes having a volume of 10×10 μm, is preferably at most 30%, preferably at most 25 or 20%, particularly preferably at most 10, 5 or 3%.

The homogeneous distribution of the surface-active substance is ensured by the manner of preparation of the feed additive.

The particle density of the feed additive is preferably at least 1.20 g/cm$^3$, particularly preferably 1.20 to 1.30 g/cm$^3$, especially preferably 1.20 to 1.26 g/cm$^3$.

The bulk density of the feed additive is preferably at least 600 kg/m$^3$, particularly 600 to 800 kg/m$^3$.

The bulk density is preferably determined as follows: An empty measuring cylinder (250 ml volume) is placed on a balance, filled with the granular product and the weight per unit volume is then determined.

To determine the particle density, the void spaces in the measuring cylinder are filled with methanol. The void volumes can thus be determined by the increase in weight and the known density of methanol (0.7918 g/ml). The difference between total volume and the volume of the methanol gives the particle volume. The particle density is then obtained, by basing the weight of the particle previously determined not on the total volume of the measuring cylinder but on the particle volume determined.

Alternatively, the particle density can also be determined using a pycnometer. The particle density is determined in this case by gas displacement. Inert gases such as helium or nitrogen are preferably used as displacement medium. A commercially available pycnometer in this connection, for example, is the helium pycnometer AccuPyc 1340 (mimetrics).

Granular feed additives according to the invention are preferably characterized in that they comprise the L-amino acid L-lysine, wherein said L-amino acid is preferably present at least in part as a sulphate salt, in which the molar ratio of sulphate to L-lysine is preferably at least 0.5, particularly preferably 0.8 to 1.2.

In the preferred embodiment in which the L-amino acid is L-lysine, feed additives according to the invention preferably have a pH of 3.5 to 6.5, particularly 4.0 to 5.0, preferably 4.2 to 4.8, measured in aqueous suspension. For measurement of the pH, a 10% by weight suspension in deionized water is prepared and the pH measured with a pH electrode at 25° C. The measured value becomes constant after ca. 1 minute.

The water content of the feed additive according to the invention is preferably between 0.1% by weight and no more than 5% by weight. The water content is preferably at most 4% by weight, particularly preferably at most 3% by weight and especially preferably at most 2.5% by weight. Water contents of at most 2% by weight are also possible.

Feed additives according to the invention are further preferably characterized in that they have a very compact structure, wherein "compact structure" is understood to mean that they have relatively few cavities. This is not least as a result of the use of the surface-active substance. Feed additives according to the invention are preferably characterized in that they have cavities less than 25% by volume, particularly less than 20% by volume, particularly preferably less than 15% by volume, especially preferably less than 10% by volume.

The present invention further relates to the use of a granular feed additive according to the invention for preparing feed additives.

Preparation of the Fermentation Broth Containing L-Amino Acid

The preparation by fermentation of L-amino acids such as L-lysine, L-methionine, L-threonine, L-tryptophan, L-valine, particularly L-lysine, is achieved by cultivation by fermentation of an amino acid-overproducing bacterial strain. The fermentation is preferably conducted with coryneform bacteria, particularly from the genus *Corynebacterium*, particularly preferably of the type *Corynebacterium glutamicum*, and/or from the genus *Escherichia*, particularly preferably of the type *Escherichia coli*, by a so-called fed-batch process (feed processes). Alternatively, the fermentation can also be carried out continuously or batchwise in a batch process (batch cultivation) or repeated fed batch process (repetitive feed processes) with the aim to produce L-amino acids (particularly L-lysine). The fermentation medium used is optimized according to the requirements of the respective production strain. A general review of known cultivation methods is available in the textbook by Chmiel (Bioprozesstechnik 1. Einführung in die Bioverfahrenstechnik [Bioprocess technology 1. Introduction to Bioprocess Technology] (Gustav Fischer Verlag, Stuttgart, 1991)) or in the textbook by Storhas (Bioreaktoren und periphere Einrichtungen [Bioreactors and Peripheral Devices] (Vieweg Verlag, Braunschweig/Wiesbaden, 1994)).

The culture medium or fermentation medium to be used has to satisfy the demands of the particular strains in a suitable manner. Descriptions of culture media of different microorganisms are present in the handbook "Manual of Methods for General Bacteriology", of the American Society for Bacteriology (Washington D.C., USA, 1981). The terms culture medium and fermentation medium or medium are mutually interchangeable.

The carbon sources used may be sugars and carbohydrates such as glucose, sucrose, lactose, fructose, maltose, molasses, sucrose-containing solutions from sugarbeet or sugarcane production, starch, starch hydrolysate and cellulose, oils and fats such as soybean oil, sunflower oil, groundnut oil and coconut fat, fatty acids such as palmitic acid, stearic acid and linoleic acid, alcohols such as glycerol, methanol and ethanol and organic acids such as acetic acid. These substances may be used individually or as a mixture.

The nitrogen sources used may be organic nitrogen-containing compounds such as peptones, yeast extract, meat extract, malt extract, corn steep liquor, soybean meal and urea or inorganic compounds such as ammonia, ammonium sulphate, ammonium phosphate, ammonium carbonate and ammonium nitrate, preferably ammonia or ammonium sulphate. The nitrogen sources may be used individually or as a mixture.

The phosphorus sources used may be phosphoric acid, potassium dihydrogen phosphate or dipotassium hydrogen phosphate or the corresponding sodium-containing salts.

The culture medium must additionally contain salts, for example in the form of sulphates of metals such as sodium, potassium, magnesium, calcium and iron, for example magnesium sulphate or iron sulphate, which are needed for growth. Finally, essential growth factors such as amino acids, for example homoserine, and vitamins, for example thiamine, biotin or pantothenic acid, may be used in addition to the substances mentioned above. Moreover, suitable precursors of the particular amino acid can be added to the culture medium. The feedstocks mentioned may be added to the culture in the form of a single mixture or may be fed in during the cultivation in a suitable manner.

For pH control of the culture, basic compounds such as sodium hydroxide, potassium hydroxide, ammonia or aqueous ammonia, preferably ammonia or aqueous ammonia, or acidic compounds such as phosphoric acid or sulphuric acid, are used in a suitable manner. The pH is generally adjusted to a value of 6.0 to 9.0, preferably 6.5 to 8.

To control the evolution of foam, it is possible to use antifoams, for example fatty acid polyglycol esters. To maintain the stability of the plasmids, suitable selective substances, for example antibiotics, can be optionally added to the medium. In order to maintain aerobic conditions, oxygen or oxygenous gas mixtures, for example air, are introduced into the culture. The use of liquids enriched with hydrogen peroxide is likewise possible.

If appropriate, the fermentation is conducted at elevated pressure, for example at a pressure of 0.03 to 0.2 MPa. The temperature of the culture is normally 20° C. to 45° C. and preferably 25° C. to 40° C. In batch processes, the cultivation is continued until a maximum of the desired amino acid has formed. This aim is normally achieved within 10 hours to 160 hours. In continuous processes, longer cultivation times are possible. To ferment suitably large production fermenter volumes of several hundred cubic metres, a plurality of upstream growth fermenter steps with successively increasing fermenter volumes are necessary.

Examples of suitable fermentation media are found, inter alia, in the patent specifications U.S. Pat. Nos. 5,770,409, 5,840,551 and 5,990,350, 5,275,940 or U.S. Pat. No. 4,275,157. Further examples of fermentation media are found in Ozaki and Shiio (Agricultural and Biological Chemistry 47(7), 1569-1576, 1983) and Shiio et al. (Agricultural and Biological Chemistry 48(6), 1551-1558, 1984). Methods for determining L-lysine and other L-amino acids are known from the prior art. The analysis can proceed, for example, as described in Spackman et al. (Analytical Chemistry, 30, (1958), 1190) by anion-exchange chromatography with subsequent ninhydrin derivatization, or it can proceed via reversed-phase HPLC, as described by Lindroth et al. (Analytical Chemistry (1979) 51: 1167-1174).

The fermentation broth thus produced is subsequently processed in accordance with the invention.

The biomass or the fermentation broth comprising biomass is preferably thermally inactivated during a suitable method step before the biomass is completely or partially removed.

Preferred Method Procedure in the Production of L-Lysine

In the case that the L-amino acid produced is L-lysine, an additional process step is preferably carried out, as already mentioned previously, which is carried out before the start of the drying process, in which ammonium sulphate and/or sulphuric acid are added to the fermentation broth, in order to establish a molar ratio of sulphate/L-amino acid of at least 0.5. The molar ratio of sulphate/L-lysine is preferably in this case at least 0.6, 0.8, 0.9 or 0.95, particularly 0.85 to 1.2, preferably 0.9 to 1.1, particularly preferably >0.95 to <1.1.

The molar ratio V of sulphate/L-lysine is calculated according to the formula: $V=2\times[SO_4^{2-}]/[L\text{-lysine}]$.

This formula takes into account that the sulphate anion is divalent. A ratio $V=1$ means that a stoichiometric compound $Lys_2(SO_4)$ is present, while a ratio of $V=0.9$ means a 10% stoichiometric amount of sulphate is present and a ratio of $V=1.1$ means a 10% excess of sulphate is present.

Alternatively, it is possible to carry out the fermentation in the presence of an amount of ammonium sulphate such that, on completion of the fermentation, a sulphate/L-amino acid ratio is already present which is in the preferred range according to the invention. In this case, the additional process step can be dispensed with.

Finally, the broth may also be used preferably with sodium bisulphite (sodium hydrogen sulphite) or another salt, for example ammonium, alkali metal or alkaline earth metal salt of sulphurous acid, which leads to stabilization and brightening of the product.

In this context, a particularly preferred method according to the invention comprises the following steps:
  providing a fermentation broth containing L-lysine;
  partially or completely removing the biomass, preferably removing at least 50 or 60% by weight, particularly preferably at least 90 or 95% by weight, of the biomass;
  optionally measuring the ratio of sulphate to L-lysine;
  subsequently optionally adding ammonium sulphate and/or corn steep liquor;
  optionally adding sulphuric acid;
  adjusting the pH, by adding sulphuric acid, to 4.0 to 6.5, particularly 4.9 to 5.1, wherein, by adding the sulphate-containing compound in the steps mentioned above, a ratio of sulphate/L-amino acid in the broth is set to 0.85 to 1.2, particularly preferably 0.9 to 1.0, particularly preferably >0.9 to <0.95;

optionally concentrating the fermentation broth to a water content of 35 to 70% by weight, particularly 35 to 50% by weight;

adding a surface-active component, such that a content of surface-active component of 0.025 to 20% by weight, particularly 0.1 to 20% by weight, preferably 0.2 to 15% by weight, particularly preferably 0.3 to 10% by weight, is set;

drying of the mixture to give a particulate composition, preferably by spray granulation;

optionally coating the particle after step with an edible oil, wherein particles are obtained which are completely or partially coated with the edible oil.

Sulphate-containing compounds in the context of the method steps mentioned above particularly relate to ammonium sulphate and sulphuric acid. In this manner, a product is obtained with an L-amino acid content (particularly L-lysine) of 10 to 70% by weight (calculated as amino acid, based on the total amount) and in the case that the L-amino acid is L-lysine, L-lysine is present in a molar ratio of sulphate/L-lysine of at least 0.5, preferably 0.6, 0.8, 0.9, 0.95, 1.0, 1.05, 1.1, 1.2, more preferably 0.85 to 1.2, preferably 0.9 to 1.1, particularly preferably >0.95 to <1.1.

If acid is added beyond the pH reduction according to the invention, increased amounts of acid are necessary due to the buffering effect of the compounds present in the broth, which may then lead to an undesired denaturation and dissolution of the coryneform bacterial cells.

In a method variant according to the invention, one or more of the salts of sulphurous acid (sulphites), selected from the group consisting of ammonium salt, alkali metal salt, and alkaline earth metal salt, is added to the fermentation broth in an amount of 0.01 to 0.5% by weight, preferably 0.1 to 0.3% by weight, particularly preferably 0.1 to 0.2% by weight, based on the fermentation broth. Preference is given to using alkali metal hydrogen sulphite, particularly preferably sodium hydrogen sulphite.

The sulphites, particularly sodium hydrogen sulphite, are preferably added as a solution before concentrating the fermentation broth. The amount used is preferably considered when adjusting the sulphate/L-amino acid ratio.

In the method according to the invention for preparing feed additives containing L-amino acids (particularly L-lysine), those procedures are preferred in which products are obtained comprising constituents of the fermentation broth.

WORKING EXAMPLES

Example 1

Influence of Biomass Content and Content of Surface-Active Substance on the Ability of the Fermentation Broth to be Granulated Fermentation broth containing lysine sulphate was provided and the biomass was removed therefrom by ultrafiltration. The fractions thereby obtained (biomass concentrate and biomass-free permeate) were then combined with one another in various proportions in order to obtain specific fermentation broths with differing biomass content. Fermentation broths having a biomass content of 0; 0.4; 3.1; 3.6; 7.1; 8.8; 10.4 and 12.0% by weight were prepared in this way.

Furthermore, fermentation broths with no biomass and fermentation broths having a biomass content of 3.1 or 12.0% by weight were treated with various amounts of corn steep liquor. Corn steep liquor comprises lecithin as surface-active component. Corn steep liquor was added to the biomass-free fermentation broth in amounts of 0; 1.0; 2.3 and 4.6% by weight, and to the fermentation broth containing 3.1 and 12.0% biomass in an amount of 2.3% by weight respectively.

A fluidized bed spray granulation was carried out using these materials. To this end, 300 g of comminuted lysine granulate were charged in each case and granulated in each case with 3800 g of fermentation broth having varying content of biomass and corn steep liquor and a dry mass of ca. 56% by weight.

The spray granulation was carried out at an inlet temperature of 150-160° C. and a fluidized bed temperature of 85° C.

After the spray granulation, the bulk density and the particle density were determined in each case.

The bulk density was determined as follows: An empty measuring cylinder (250 ml volume) was placed on a balance, filled with the granular product and the weight per unit volume was then determined.

To determine the particle density, the void spaces in the measuring cylinder were filled with methanol. The void volumes could thus be determined by the increase in weight and the known density of methanol (0.7918 g/ml). The difference between total volume and the volume of the methanol gives the particle volume. The particle density is then obtained, by basing the weight of the particle previously determined not on the total volume of the measuring cylinder but on the particle volume determined.

Result

It was found that all the mixtures investigated could be granulated. However, a stronger tendency to stickiness was observed with decreasing biomass. Surprisingly however, granulation was possible despite the complete absence of biomass, even if suitable measures may be required to control the particle size, for example, by using cutters in the fluidized bed or by external seeding. The ability to granulate in the absence of biomass was, however, very difficult.

It has now been found that the addition of corn steep liquor leads to a distinctly lower tendency to stickiness and therefore a significantly improved ability to granulate the fermentation broth. Improved properties were achieved in this case with lower amounts of corn steep liquor, since the hygroscopicity of the product increased with increasing amounts of corn steep liquor such that an amount of 1 to 3% by weight of corn steep liquor was found to be particularly advantageous in accordance with the invention with respect to storage stability.

Moreover, it has also been found, surprisingly, that the particle density is dependent on the biomass content and the surface-active substance content.

It has been shown that the particle density increased with decreasing biomass and that the particle density of the biomass-free preparation further increased continuously due to the addition of corn steep liquor. This gives rise to distinct advantages in packing and transport costs.

The results of the measurements are shown in the following tables.

TABLE 1

Dependency of the particle density and bulk density
on the biomass content in the starting fermentation broth.

| Biomass [% by weight] | Particle density [g/l] | Bulk density [g/l] |
|---|---|---|
| 10.4 | 1113 | 613.2 |
| 8.8 | 1123 | 607.6 |
| 7.1 | 1118 | 620.4 |
| 3.6 | 1172 | 632.8 |
| 0.4 | 1185 | 636.4 |
| 0.0 | 1182 | 634.8 |

The second experimental series showed that the particle density after the removal of biomass may be further increased by the addition of CSL. This effect is also observed in the presence of biomass but is less strongly pronounced. The higher the amount of biomass remaining, the lower the particle density which can be achieved, which can be seen in Table 2.

TABLE 2

Dependency of the particle density of the granulate
on the content of biomass and corn steep liquor (CSL) in the
starting fermentation broth.

| Biomass [% by weight] | CSL content [% by weight] | Particle density [g/l] |
|---|---|---|
| 0.0 | 0.0 | 1212 |
| 0.0 | 1.0 | 1217 |
| 0.0 | 2.3 | 1233 |
| 0.0 | 4.6 | 1250 |
| 3.1 | 2.3 | 1177 |
| 12.0 | 2.3 | 1168 |

The invention claimed is:

1. A method for preparing a feed additive, comprising the following steps:
   a) obtaining a low biomass content fermentation broth by:
      i) fermenting an L-amino acid-producing microorganism in an aqueous culture medium to produce a fermentation broth;
      ii) after the fermenting of step i) is complete:
         aa) removing biomass from the fermentation broth to reduce the biomass content to, at most, 4% by weight;
         bb) adding surface-active substance to the fermentation broth to a final concentration of 0.025 to 20% by weight; and
   b) drying the low biomass content fermentation broth obtained in step a) in order to convert it into said feed additive;
   wherein the concentrations of biomass and surface-active substance in the low biomass content fermentation broth are such that the feed additive of step b) is a particulate composition with a particle density of at least 1.20 g/cm$^3$.

2. The method of claim 1, wherein the concentrations of biomass and surface-active substance in the low biomass content fermentation broth are such that the feed additive of step b) is a particulate composition with a particle density of 1.20-1.30 g/cm$^3$.

3. The method of claim 1, further comprising completely or partially coating the particulate composition with an edible oil.

4. The method of claim 1, wherein the L-amino acid is L-lysine, L-methionine, L-threonine, L-valine or L-tryptophan.

5. The method of claim 1, wherein the amino acid is L-lysine and wherein, in a step after completion of fermentation and before the start of drying, ammonium sulphate and/or sulphuric acid is added to the fermentation broth in order to establish a sulphate/L-amino acid ratio of 0.85 to 1.2.

6. The method of claim 1, wherein at least 30% by weight of the biomass is removed from the fermentation broth before drying.

7. The method of claim 1, wherein the surface-active substance is selected from the group consisting of: corn steep liquor; lipids; antifoaming agents; surfactants; and mixtures thereof.

8. The method of claim 1, wherein the surface-active substance is an antifoaming agent selected from the group consisting of: polysiloxanes; mono- and polyglycols; phospholipids; and fatty acid glycerides.

9. The method of claim 1, wherein the fermentation broth used in the drying comprises:
   a) an L-amino acid content, as amino acid base, of 12 to 48% by weight;
   b) a solids content, including biomass, of 20 to 60% by weight;
   c) a surface-active substance content of 0.025 to 20% by weight;
   d) a sulphate to L-amino acid ratio of 0.8 to 1.2; and
   e) a pH of 3.5 to 7.0.

10. The method of claim 1, wherein drying is conducted by spray-drying.

11. The method of claim 1, wherein the fermentation broth used in the drying step comprises:
   a) a biomass content of at most 1% by weight;
   b) an L-lysine content, as amino acid base, of 12 to 48% by weight;
   c) a solids content, including biomass, of 30 to 50% by weight;
   d) a surface-active substance content of 0.3 to 10% by weight;
   e) a sulphate to L-lysine ratio of 0.8 to 1.2; and
   f) a pH of 4.0 to 5.0.

12. The method of claim 1, wherein:
   a) at least 50% by weight of the biomass is removed from the fermentation broth before drying;
   b) the surface-active substance is present in the fermentation broth before drying in an amount of 0.3 to 10% by weight;
   c) drying is conducted by spray granulation using a fluidized bed reactor;
   d) the L-amino acid is L-lysine.

13. The method of claim 12, further comprising completely or partially coating the particulate composition with an edible oil.

14. The method of claim 13, wherein, in a method step after completion of the fermentation and before the start of the drying, ammonium sulphate and/or sulphuric acid is added to the fermentation broth in order to establish a sulphate/L-amino acid ratio of 0.85 to 1.2.

15. The method of claim 14, wherein at least 70% by weight of the biomass is removed from the fermentation broth before drying and wherein said feed additive is a particulate composition with a particle density of 1.20-1.30 g/cm$^3$.

16. The method of claim 15, wherein at least 90% by weight of the biomass is removed from the fermentation broth before drying.

17. The method of claim 1, wherein the fermentation broth is converted directly into a granulate in one process step, and wherein the granulate comprises: 40-60% L-lysine; a mean particle diameter of 60-1500 μm; a biomass content of 0.1-2% by weight; a surface-active substance content of 0.5 to 15% by weight; and a water content of at most 3.5% by weight.

18. A method for preparing a feed additive, comprising the following steps:
- a) fermenting an L-amino acid acid-producing microorganism in an aqueous culture medium to produce a fermentation broth;
- b) after the fermenting of step a) is complete, converting the fermentation broth into a low biomass content fermentation broth by:
  - i) removing biomass from the fermentation broth to reduce the biomass content to, at most, 4% by weight, wherein at least 50% by weight of the biomass is removed from the fermentation broth before drying;
  - ii) adding a surface-active substance to the fermentation broth, wherein said surface-active substance is added to a final concentration of 0.025 to 20% by weight; and
- c) drying the low biomass content fermentation broth obtained in step b) to convert it into a said feed additive;

wherein the concentrations of biomass and surface-active substance in the low biomass content fermentation broth are such that the feed additive of step c) is a particulate composition with a particle density of 1.20-1.30 g/cm$^3$.

19. The method of claim 18, wherein, in a step after completion of fermentation and before the start of drying, ammonium sulphate and/or sulphuric acid is added to the fermentation broth in order to establish a sulphate/L-amino acid ratio of 0.85 to 1.2.

20. The method of claim 18 wherein, said L-amino acid is L-lysine and said surface-active substance is selected from the group consisting of: corn steep liquor; lipids; antifoaming agents; surfactants; and mixtures thereof.

* * * * *